United States Patent [19]
Hatcher

[11] Patent Number: 5,474,573
[45] Date of Patent: Dec. 12, 1995

[54] TOGGLE SUTURE HANDLING MEANS AND METHOD

[76] Inventor: Charles W. Hatcher, 6561 Arno Rd., College Grove, Tenn. 37046

[21] Appl. No.: 293,442

[22] Filed: Aug. 22, 1994

[51] Int. Cl.⁶ .................................................. A61B 17/04
[52] U.S. Cl. ...................... 606/232; 606/139; 128/898
[58] Field of Search ............................... 606/213, 215, 606/230, 216, 228–232; 604/51, 60; 128/898

[56] References Cited

U.S. PATENT DOCUMENTS

| | | | |
|---|---|---|---|
| 4,669,473 | 6/1987 | Richards et al. | 606/232 |
| 4,741,330 | 5/1988 | Hayhurst | 606/232 |
| 5,053,046 | 10/1991 | Janese | 606/215 |

Primary Examiner—Gary Jackson
Attorney, Agent, or Firm—E. Strickland

[57] ABSTRACT

Disclosed is a method of suturing the abomasum of a ruminant animal. The method includes inserting one end of a cannula through the belly of the animal and into the lumen of the abomasum. One end of a suture and toggle attached thereto is inserted through a bore of the cannula and into the lumen by travel of a trocar through the bore behind the toggle. The extent of the travel of the cannula into the lumen is limited by providing an outer end of the cannula with a flange that engages the hide of the animal and the travel of the trocar through the bore of the cannula is limited by providing the trocar with a handle that abuts against the flange of the cannula.

2 Claims, 2 Drawing Sheets

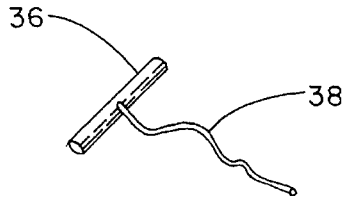
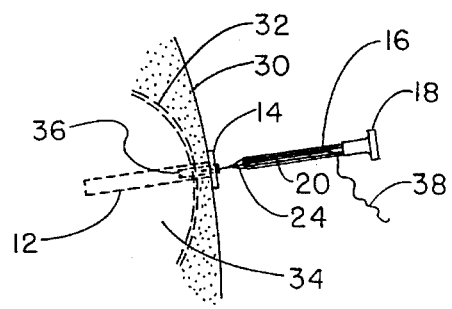
FIG 5  FIG 6
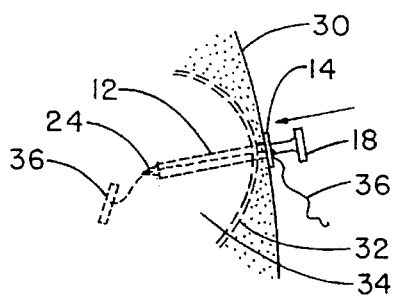
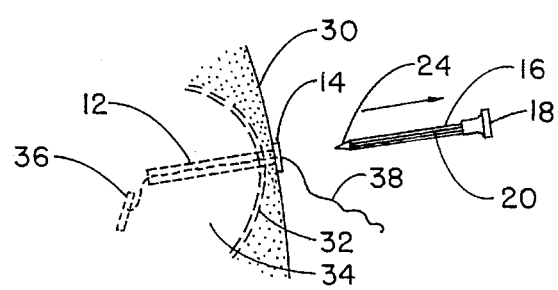
FIG 7  FIG 8
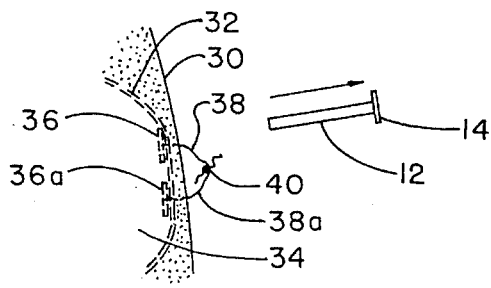
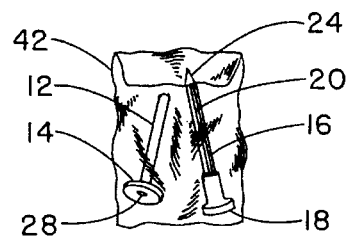
FIG 9  FIG 10
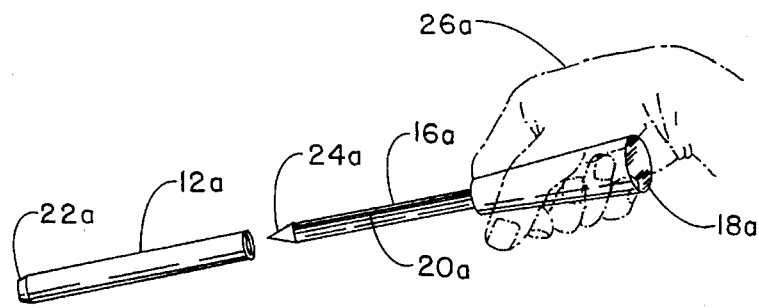
PRIOR ART
FIG 11

5,474,573

TOGGLE SUTURE HANDLING MEANS AND METHOD

BACKGROUND OF THE INVENTION

1. Field of the Invention

This invention relates to veterinary operations and an instrument for surgical stitching or suturing the stomach wall to the outside hide of an animal at the lower right ventral quadrant. This procedure connects a left displaced abomasum.

2. Description of the Prior Art

Heretofore, the operating device for use in suturing the stomach of a ruminant animal, such as a cow, was basically comprised of a trocar or solid cylindrical member fitted inside a hollow tube or cannula. The cannula was inserted through the hide of the animal via a small incision and into the lumen of the abomasum. The difficulty with such a device is that the cannula sometimes slips through the hide of the animal and into the lumen of the abomasum or loose into the body cavity.

SUMMARY OF THE INVENTION

I have found that by providing the outside end of a cannula with an outwardly extending flange or circular disc and inserting the other end of the cannula and trocar through a small cut made in the hide of the animal, the flange or disc engages the hide of the animal and is thereby prevented from slipping through the hide and into the animal's stomach (lumen). Such a cannula can then be used to insert a suture and toggle without concern of the cannula slipping into the stomach. The trocar is prevented from traveling beyond the flange of the cannula since the trocar has a handle that is larger than the bore of the cannula through which the trocar end and a toggle enter the stomach.

BRIEF DESCRIPTION OF THE DRAWINGS

For a better understanding of my invention, reference will now be made to the drawings in which:

FIG. 5 is a perspective view of a toggle-suture such as may be used with the trocar and cannula in the manner shown in FIGS. 6 to 9, FIG. 6 depicts the manner in which a suturing procedure is begun by using the trocar-cannula by lining up the suture in a groove of the trocar and inserting it into the cannula, FIG. 7 illustrates the manner in which the trocar pushes the toggle suture through the cannula, FIG. 8 shows the trocar pulled back leaving the toggle inside the lumen of the abomasum and connected to one end of the suture, the other end of the suture being outside the skin or hide of the animal.

FIG. 9 shows completion of the suture process with two sutures tied together and two toggles pulled against the inside wall of the abomasum, FIG. 10 depicts a trocar and cannula of the invention located inside a package such as a plastic envelope, preferably clear, ready for sale to a potential user, who can purchase the toggle-suture (one or more) either as a part of a kit or buy one or more separately.

FIG. 11 shows a prior art trocar-cannula in use with no disc or flange and with a grip-type handle at one end of the trocar.

DETAILED DESCRIPTION OF THE PREFERRED EMBODIMENTS OF THE INVENTION

Figure 1:
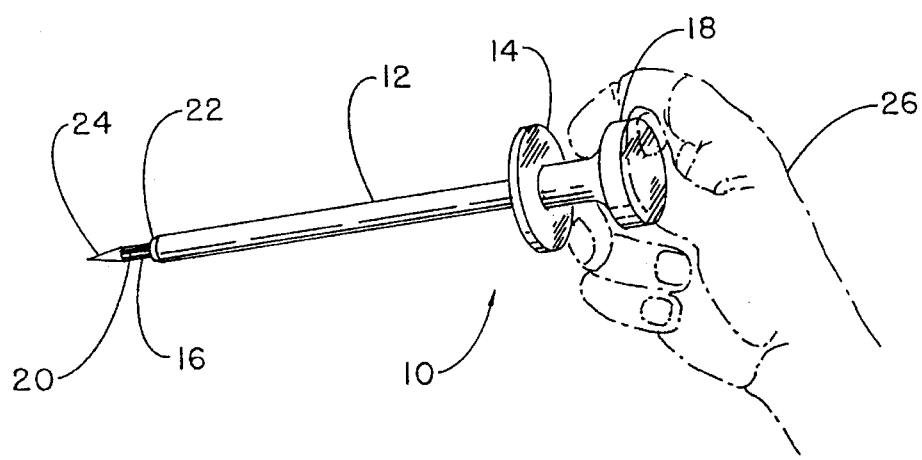
FIG. 1 is a perspective view of the toggle/suture handling assembly of the invention (cannula and trocar assembled together); a human hand shown holding a handle portion of the trocar.

Referring now to FIG. 1 of the drawings, a surgical device 10 is depicted in a perspective view, the device including a somewhat elongated cannula or tube 12 of substantially constant outside and inside bore diameter, the cannula including, in addition, a generally circular disc flange 14 for abutting against the outside hide (30 in FIGS. 3 and 4) of an animal. A trocar or shaft 16 is inserted through the bore 28 of the cannula by grasping a handle 18 thereof, as shown in FIG. 1. The trocar has a shank that is generally constant in cross section and sized slightly smaller than the bore of the cannula. The shank is provided with a narrow groove 20 and terminates in a pointed end 24, the groove extending from handle 18 to the pointed end. The cannula is provided with a beveled end 22 that is located behind 24 when the trocar is inserted completely through the cannula. A hand 26 of a user of assembly 10 is also shown in FIG. 1.

Figure 2:
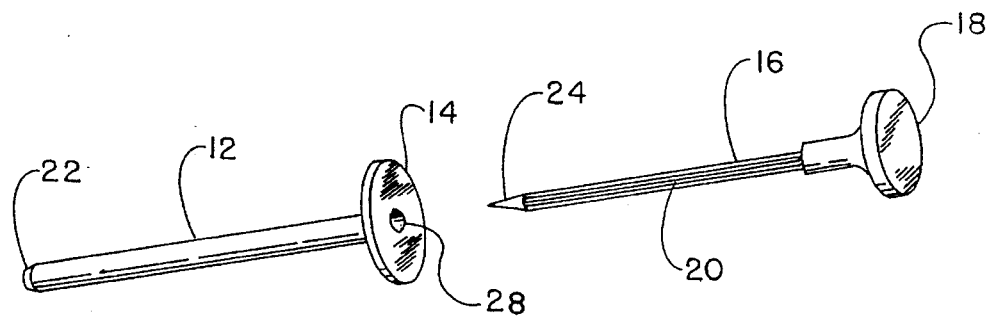
FIG. 2 is a perspective view showing the two major components (the trocar and a cannula in separated portions) of the toggle-suture handling device of the invention.

In FIG. 2 of the drawings, the bore of cannula 12 is labelled 28 and is sized to stop handle 18 from traveling through the bore, the handle being larger in cross section than the bore.

Figure 3:
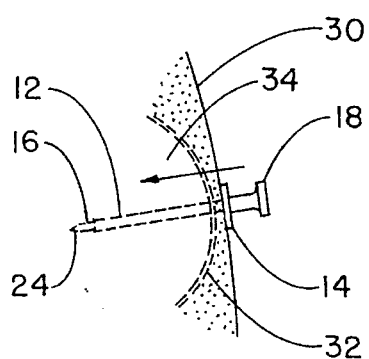
FIG. 3 is a somewhat schematic view showing insertion of the trocar and the cannula through the outside hide, subcutaneous tissue and into the cow's stomach (abomasum), the cannula having a disc or flange which rests against the outside skin or hide of the animal.
Figure 4:
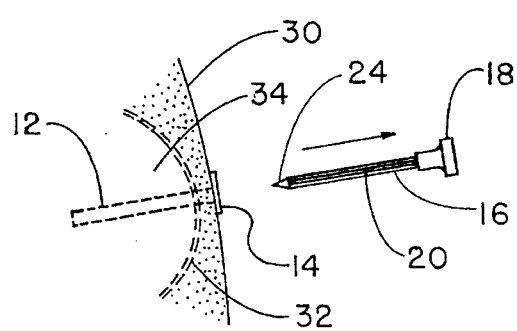
FIG. 4 depicts the trocar after it has been removed from the cannula which is still located in the lumen of the abomasum.

FIG. 3 of the drawings shows the cannula and trocar inserted through the hide 30 of an animal (not otherwise shown) and through the wall 32 of the animal's abomasum or stomach 34. Pointed end 24 of the trocar and end 22 of the cannula are entered into the hide 30 through a small cut (not shown) in the animal's hide and the trocar removed from the cannula, as shown in FIG. 4, leaving the cannula in place. The pointed end 24 of the trocar punctures wall 32 of the abomasum.

FIG. 5 of the drawings shows a toggle 36 and a suture 38 attached thereto. The toggle is inserted into the end of cannula located outside the animal and the suture is placed in groove 20 of the trocar shank, its loose end lying near the trocar handle. The trocar is next inserted into the cannula behind the toggle, the pointed end of the trocar moving the toggle and suture through the bore of the cannula and into lumen 34. FIG. 6 shows the trocar before the toggle is pushed through the cannula bore, while FIG. 7 shows the trocar fully inserted in the cannula, the cannula remaining in place in the animal's abdomen and stomach. As seen further in FIG. 7, the loose end of the suture is located outside of the animal.

The trocar is now removed from the cannula (FIG. 8) leaving the suture accessible for tying the toggle against the hide of the animal, as seen in FIG. 9 of the drawings, and thereby securing the stomach wall to the belly of the animal. This, of course, requires removal of the cannula from the animal, as shown in FIG. 9.

Two such toggles 36 and 36a and sutures 38 and 38a are shown in FIG. 9, with the two sutures tied together at 40. The two toggles are pulled back against the wall of the abomasum of the animal by the sutures, securing the abomasum to the belly of the animal.

This procedure, as thus far described, is simple and reliable, and the cannula remains in place after being inserted through the hide and abomasum until removed. As seen in FIG. 11 of the drawings, prior cannulas 12a had no external flange or disc to prevent the cannula from entering completely into the animal.

FIG. 10 of the drawings shows the cannula and trocar of the invention packaged together in a container 42 as a kit. One can purchase the kit, which is ready for use by a veterinarian.

While the invention has been described in terms of preferred embodiments, the claims appended hereto are intended to encompass all embodiments which fall within the spirit of the invention.

What is claimed is:

1. A method of suturing the abomasum of a ruminant animal comprising:

inserting one end of a cannula through the hide of the animal and into its lumen through a wall of the abomasum;

inserting one end of a suture and toggle attached thereto in a bore of the cannula and directing the toggle into the lumen of the animal by travel of a forward pointed end of a trocar through said bore behind the toggle, the trocar having an axial slot for receiving the suture and containing it in and along the length of the cannula, and the cannula having an outer end for location outside of the animal;

limiting the extend of the travel of the cannula into the lumen by providing the outer end of the cannula with an integral flange that engages the hide of the animal and prevents the cannula from slipping completely into the lumen;

limiting the travel of the trocar through the bore of the cannula by providing the trocar with a handle that abuts against the flange of the cannula after the toggle clears the cannula in the lumen and the forward end of the trocar behind the toggle enters the lumen beyond the end of the cannula;

removing the cannula and trocar from the lumen; and using the toggle and suture to tie the stomach wall of the animal to its side.

2. The method of claim 1 including:

inserting a second suture and toggle in the lumen of the animal using the steps of claim 1 and in a manner that locates the two sutures with ends located outside of the animal; and tying the outside ends of the two sutures together to secure the wall of the abomasum to one side of the animal.

\* \* \* \* \*